(12) United States Patent
Oviatt et al.

(10) Patent No.: US 7,422,607 B2
(45) Date of Patent: Sep. 9, 2008

(54) ANTI-CALCIFICATION TREATMENTS FOR HEART VALVES AND VASCULAR GRAFTS

(76) Inventors: Henry W. Oviatt, 45449 Camino Monzon, Temecula, CA (US) 92592; Neal K. Vail, 118 E. Mulberry, San Antonio, TX (US) 78212

(*) Notice: Subject to any disclaimer, the term of this patent is extended or adjusted under 35 U.S.C. 154(b) by 609 days.

(21) Appl. No.: 11/209,550

(22) Filed: Aug. 23, 2005

(65) Prior Publication Data

US 2006/0047343 A1    Mar. 2, 2006

Related U.S. Application Data

(60) Provisional application No. 60/604,178, filed on Aug. 24, 2004.

(51) Int. Cl.
*A61F 2/02* (2006.01)
*A61F 2/76* (2006.01)

(52) U.S. Cl. .................. 8/94.11; 8/94.2; 623/11.11; 623/901; 623/915; 623/920

(58) Field of Classification Search .............. 8/94.11, 8/94.2; 623/11.11, 901, 915, 920
See application file for complete search history.

(56) References Cited

U.S. PATENT DOCUMENTS

2003/0072677 A1* 4/2003 Kafesjian et al. .............. 422/33
2004/0093674 A1* 5/2004 Cunanan et al. .............. 8/94.11

* cited by examiner

*Primary Examiner*—Lorna M. Douyon
*Assistant Examiner*—Amina Khan
(74) *Attorney, Agent, or Firm*—G.L. Loomis & Associates, Inc.; Gary L. Loomis

(57) ABSTRACT

The present invention provides processes for fixation of biological tissue and/or post-fixation treatment of such tissue that result in modified tissues with reduced susceptibility to in vitro calcification when used in prosthetic devices. The invention also relates to calcification resistant biological tissue and to methods of using such tissue.

14 Claims, 1 Drawing Sheet

ANTI-CALCIFICATION TREATMENTS FOR HEART VALVES AND VASCULAR GRAFTS

RELATED U.S. APPLICATION DATA

Provisional application No. 60/604,178, filed on Aug. 24, 2004.

FIELD OF THE INVENTION

The instant invention relates to the field of prosthetic device development. More particularly, it relates to processes for the treatment of biological tissue for use in prosthetic devices in order to prevent calcification of the treated tissue during use of the devices.

BACKGROUND OF RELATED ART

The surgical implantation of prosthetic devices (prostheses) into humans and other mammals has been carried out in recent years with increasing frequency. Such prostheses include, by way of illustration only, heart valves, vascular grafts, urinary bladders, heart bladders, left ventricular-assist devices, hip prostheses, SILASTIC™ breast implants, tendon prostheses, and the like. They may be constructed from natural tissues, inorganic materials, synthetic polymers, or combinations thereof.

By way of illustration, mechanical heart valve prostheses typically are composed of rigid materials, such as polymers, carbons, and metals, and employ a poppet occluder which responds passively with changes in intracardiac pressure or flow. Valvular bioprostheses, on the other hand, are typically fabricated from either porcine aortic valves or bovine pericardium. In either case, the tissue is fixed and then sewn onto a flexible metallic alloy or polymeric stent that is subsequently covered with a poly(ethylene terephthalate) cloth sewing ring covering.

Prostheses derived from natural tissues are preferred over mechanical devices because of certain significant clinical advantages. Tissue-derived prostheses generally do not require routine anticoagulation. Moreover, when they fail, they usually exhibit a gradual deterioration that can extend over a period of months or even years. Mechanical devices, on the other hand, typically undergo catastrophic failure, sometimes with fatal consequences.

Tissue valves typically are made from either porcine (pig) valves dissected from pig hearts, manufactured from the bovine (cow) pericardial sac material, or homografts made from human cadaver tissue. Porcine and bovine tissue must be rendered stable to enzymatic and hydrolytic degradation to achieve long-term implant stability. Current manufacturers stabilize these tissues by soaking the tissue in a dilute solution of a reactive compound, the most common being 1,5-pentane dialdehyde (glutaraldehyde). Alternate methods of fixation have been investigated and patented, most of which attempt to address the issues of calcification of glutaraldehyde fixed valves discussed below, though few have found widespread acceptability in the heart valve marketplace.

A challenge with glutaraldehyde fixed tissues is the propensity for these materials to calcify (Schoen et al. 1988, Levy et al. 1986, Bruck 1981). There is a greatly increased incidence of calcium deposit formation (calcification) that occurs on tissue valves after glutaraldehyde fixation (Levy et al. 1986; Schoen et al. 1992). While any prosthetic device can fail because of mineralization, and especially calcification, this cause of prosthesis degeneration is especially significant for tissue-derived prostheses. Indeed, calcification has been stated to account for over 60 percent of the failures of cardiac bioprosthetic valve implants. Despite the clinical importance of the problem, the pathogenesis of calcification is incompletely understood:

Numerous investigators have attempted to reduce calcification by various methods (Pathak et al. 1991, Vyavahare et al. 1997). A number of post fixation treatments have been attempted and patented, such as treatment with non-native alpha amino acids (U.S. Pat. No. 4,976,733; Girardot et al. 1994), low molecular weight aliphatic diamine treatment (Zilla et al. 2001), ethanol extraction (Vyavahare et al. 1997), surfactant extraction (Paez et al. 2000), and a host of other approaches. These examples are given for illustrative purposes and are in no way intended to be exhaustive of the currently patented methods. To date, the most successful of these methods are those patented by Giradot (U.S. Pat. No. 4,976,733, the entire contents of which are incorporated herein by reference); marketed by Medtronic in the Medtronic FREESTYLE™ and MOSAIC™ heart valve product lines. U.S. Pat. No. 4,976,733, in particular, addresses alpha amino oleic acid as the preferred treatment for tissue valves to block free aldehyde sites on glutaraldehyde fixed tissue that are thought by many to be the main culprit in the onset of calcification of tissue heart valves. A particular challenge with the post-fixation treatment method described by Giradot is the extremely low solubility of the preferred alpha amino oleic acid compound in the buffer system described.

Supercritical fluids have been investigated for the treatment of biological materials for bioprosthetic devices (U.S. Pat. No. 4,749,522; Fages et al. 1995; Fages et al. 1998; WO 2002/007785). These processes focus on using the supercritical fluid media to extract components from the tissue.

Technologies that significantly reduce the calcification potential of graft tissue and allow for the creation of stabile tissue from a fixed tissue medium with an extended life over current processes are needed. In particular, the ability to make small diameter vascular grafts resistant to thrombosis and calcification is an extremely important need, especially for patients (such as diabetics) with poor vascularity, damaged saphenous veins or those who are undergoing a second bypass operation. Therefore, there is especially a need for new technologies that allow for the manufacture of small diameter vascular grafts by tissue fixation and increased durability of tissue based cardiac bioprosthetic valves.

SUMMARY OF THE INVENTION

The present invention overcomes problems in the art by providing methods for fixation of tissue s and/or post-fixation treatment of such tissue that result in tissue that is less susceptible to calcification when used in prosthetic devices. In some embodiments, these tissues are treated in a manner that places hydrophobic groups on the surface, thereby preventing calcification. The invention also relates to calcification resistant biological tissue and methods of using such tissue.

In broad embodiments, the invention relates to processes and methods comprising: providing a tissue from a natural source; fixing the tissue; and treating the tissue with an agent to prevent calcification. In some cases, the steps of fixation of the tissue and the treating of the tissue occur in the same procedure. For example, the tissue can be treated with a single compound or agent or mixture of compounds or agents that both fix the tissue and add an anti-calcification agent or chemical group to the tissue. In other cases, the tissue is first fixed using any of a number of standard fixatives and fixation procedures and then treated in a manner that adds an anticalcification agent or chemical group to the biological tissue. Some preferred methods of accomplishing these aspects of the invention are described below.

The invention, in some more specific embodiments, relates to a method of fixation where a large biocompatible hydrophobic group, for example a siloxane or a perfluorocarbon, is present within a dialdehyde or other fixative molecule and serves to reduce calcification potential while retaining biocompatibility. The invention further relates to methods of post-fixation treatment with biocompatible hydrophilic groups, for example siloxanes or perfluorocarbons, which treatment significantly reduces calcification potential of the tissue while retaining biocompatibility.

Specific embodiments of the present invention relate to method of preparing tissue, for example, tissue from animal sources, for the use in the preparation of prosthetic devices. In some general embodiments, these methods comprise: obtaining a biological tissue sample; fixing the biological tissue; and treating the biological tissue with an agent that creates a hydrophobic environment on the tissue and serves to prevent calcification of the tissue during use while retaining biocompatibility. In some embodiments, the fixing of the tissue and the treating of the tissue with the agent that creates the hydrophobic embodiment occurs in the same procedure. In such cases, the agent used to treat the tissue to prevent calcification can also fix the tissue, as is the case with the substituted dialdehyde compounds discussed below. Alternatively, mixtures comprising separate fixatives and agents that create the hydrophobic embodiment can be applied in the same step. In other embodiments, the tissue is first fixed and then treated with the agent.

The agent that creates the hydrophobic environment can be any known in the art. In some embodiments, the agent is an agent comprising a siloxane group or a perfluorocarbon group. In some broad embodiments, the invention relates to the use of siloxane-containing compounds in the preparation of biological tissues. Such siloxane-containing compounds can include, but are not limited to, siloxane dialdehydes, siloxane monoaldehydes, and siloxane diamines. For example, the advantages of the invention may be obtained by using a siloxane dialdehyde for primary fixation or a siloxane-amine or siloxane monoaldehyde as a post fixation treatment. The result of these methods is that a siloxane chain imparting a degree of hydrophobicity is placed on the tissue surface. Siloxanes are well known to be biocompatible and non-thrombogenic, and are thus ideal materials to be used for heart valve materials. In addition to reacting with residual aldehyde functional groups on the surface of the tissue, such as with a siloxane amine or diamine, the presence of the siloxane creates a hydrophobic environment on the surface of the tissue that resists the influx of calcium ions that are required for calcification.

For example, the agent can be a siloxane dialdehyde comprising a siloxane chain with terminal aldehyde groups. In some preferred embodiments, the siloxane dialdehyde, a hydrocarbon chain, further defined as is $-CH_2-CH_2-$, connects aldehyde groups to a siloxane group. Additionally, the siloxane dialdehyde may comprise at least one silicon atom comprising both an R and an R' group comprising the substituents alkyl, benzyl, phenyl, cyanoethyl, or other groups known to be present in siloxane polymers. In some specific embodiments, R and R' are both methyl groups. In some embodiments, the agent is a dialdehyde, such as, for example but not limited to, the siloxane dialdehydes discussed above, and/or a pentane dialdehyde comprising pendant side groups. For example, the dialdehyde can comprise a siloxane group that is attached to a hydrocarbon chain with chain lengths from $C_2$ to $C_{30}$. Alternatively, the dialdehyde may comprise side chains comprised of a perfluorocarbon with a carbon chain length of the perfluorocarbon from $C_1$ to $C_{30}$. In some embodiments, the side chains are aliphatic. Additionally, such aliphatic side-chains may be substituted with additional functional groups, such as naturally occurring or non-natural alpha amino acids, or aliphatic chains with unsaturation, such as are derived from alpha amino oleic acid. The agent may comprise a fluorocarbon segment comprising one or more aldehyde groups. In some embodiments, the fluorocarbon segment is a dialdehyde. The above described dialdehyde compounds provide advantages, in some embodiments, in that they can both fix tissue and created a hydrophobic environment on the surface of the tissue, thus preventing calcification of the tissue when a prosthesis is in use.

In other embodiments, the agent is a diamine or monoamine, including but not limited to a siloxane diamine or monoamine or a perfluorocarbon diamine or monoamine. For example, the siloxane diamine or monoamine comprises at least one amine group attached to the siloxane diamine via a hydrocarbon chain. In some specific embodiments, the hydrocarbon chain connecting the amine group to the siloxane group is $-CH_2-CH_2-CH_2-$. In other embodiments, the diamine or monoamine comprises a perfluorocarbon segment.

In some cases the agent does not comprise an alpha amino, and in particular, not an alpha amino oleic acid. However, in the context of some embodiments of the invention, including those relating to the use of supercritical $CO_2$ solvents, compounds comprising alpha amino acids, and, in particular alpha amino oleic acids are contemplated.

The tissue of the present invention is typically obtained from an animal. Most often, the tissue is soft tissue, although any form of tissue that is useful in any given situation may be employed. The tissue may be derived from either a human or animal, with bovine and porcine tissue being among the currently preferred commercial forms of tissues employed. Of course, those of skill will understand how to use any number of tissues from any number of species in the context of the invention, in view of the disclosure herein as discussed elsewhere in this specification. In some specific embodiments, the tissue is made from bovine pericardial tissue, while in others it is of excised porcine valve tissue. In some applications, it may be possible and/or beneficial to obtain tissue material from the subject or patient who will ultimately receive the prosthesis. In some case, the tissue is a vascular tissue. For example, the tissue can be a small diameter blood vessel. The tissue is typically fixed in a manner suitable for implantation in humans. The fixation methods employed typically stabilize the tissue from degradation from naturally circulating enzymes in the human body or other mechanisms of degradation for at least some period of time. The fixation also typically is performed in a manner wherein the tissue is fixed so as to minimize immune responses when implanted in a human body. In some preferred embodiments, the tissue is fixed with a chemical containing one or more aldehyde groups, for example but not limited to glutaraldehyde, a siloxane dialdehyde, or a perfluorocarbon dialdehyde. The tissue may be further treated in a manner wherein the tissue resists thrombosis.

During the treatment of the tissue with the fixative and/or agent, the fixative and/or agent are typically dissolved or emulsified in a medium.

In some embodiments, the medium is a supercritical medium, for example, but not limited to supercritical $CO_2$. Additionally, the invention relates to the use of supercritical fluids to incorporate new materials into tissues, particularly those that are not readily water soluble, such as alpha amino acids, and particularly non-natural long chain alpha amino acids (more than 8 carbons), and compounds containing siloxane or fluorocarbon groups that are known to have enhanced solubility in supercritical $CO_2$. This disclosure describes the use of supercritical fluid processing to fix (stabilize) animal derived tissues and reduce their calcification potential with supercritical fluid $CO_2$ as the solvent medium and an added component to fix the tissue or to block active sites in fixed tissue resulting from the fixation process. This invention is particularly advantageous for use with compounds that exhibit a high solubility in supercritical $CO_2$ such as aliphatic, functionalized aliphatic, siloxane, and fluorocarbon containing compounds. Especially applicable are the use of siloxane dialdehydes for tissue fixation instead of glutaraldehyde, and the treatment of glutaraldehyde fixed tissues with siloxane diamines to reduce the calcification potential of fixed tissue used for heart valve replacements and vascular tissue materials. Fluorosilicone dialdehydes are also expected to have high solubility in SCF $CO_2$ and can therefore be substituted for siloxane dialdehydes.

A significant advantage of a supercritical fluid process is that the solubility of compounds can be adjusted by changes in the pressure and temperature of the system. Some compounds, such as silicones and fluorocarbons are known to be very soluble in supercritical carbon dioxide ($scCO_2$). Aliphatic hydrocarbons and fatty acids have a lower solubility than silicones and perfluorocarbons in $scCO_2$, but this can be modified with pressure and temperature. A second advantage is that a supercritical system can use a compound (such as carbon dioxide) that is typically a gas at standard temperature and pressure (STP), such that the process can be considered a "green" process with a minimal waste stream. As a result, a supercritical fluid process can be used to carry a fixative agent into a tissue prostheses, then used to extract any unreacted fixative agent from the fixed tissue, without leaving residual solvent. Third, supercritical fluids have gas-like properties, such as very low viscosity and high diffusion coefficients, and, as a result, can penetrate porous systems more readily than normal condensed phase solvents. The supercritical state may therefore present a significant advantage in the penetration of tissue for fixation with a monomeric or polymeric species that can act as a fixative for the tissue.

The media of the invention under normal ambient pressure may comprise at least one alcohol, ether, polar aprotic solvent, DMSO, amide, chlorocarbon, fluorocarbon, chlorofluorocarbon, ketone, siloxane, or hydrocarbon. In some preferred embodiments, the medium comprises an ether, THF, or ethanol. The medium is often aqueous, for example, but not limited to, a combination of water and ethanol and/or water and THF.

The methods of the invention may further comprise placing the tissue in a suitable prosthetic device. Additionally, the methods of the invention may comprise placing that prosthetic device in a subject, for example a human or non-human animal subject. In some embodiments, the methods are further defined as methods of using the tissue or a prosthesis containing it to replace or augment a human heart valve or the tissue to repair a damaged vein or artery.

The invention also relates to a prosthetic device comprising fixed tissue that has been treated with an agent that creates a hydrophobic environment on the tissue and serves to prevent calcification of the tissue during use. In some cases the tissue is further defined as comprising a siloxane and/or perfluorocarbon group. For example, the siloxane and/or perfluorocarbon group may be comprised in a siloxane and/or perfluorocarbon dialdehyde. Alternatively, the siloxane and/or perfluorocarbon group can be further defined as comprised of a siloxane and/or perfluorocarbon diamine or monoamine. In some cases, the prosthesis is defined as an artificial circulatory system valve, for example but not limited to a heart valve or a venous valve. In other cases, the prosthesis is further defined as a vascular tissue. The invention contemplates any and all prostheses and/or tissues prepared according to the methods discussed above and elsewhere in this specification and any and all prostheses and/or tissues that have the physical characteristics of any tissues and/or prostheses prepared according to such methods.

The invention also relates to methods of testing tissues and procedures for preparing them, including procedures for testing new fixatives and/or agents. In this regard, those of skill in the art will, in view of the instant specification, be able to prepare and test candidate fixatives, agents, and/or methods by employing the knowledge in the art and the methodologies taught herein.

Although the primary description of the invention is been directed to the treatment of natural tissue materials where calcification is a significant problem with respect to prostheses presently being implanted, primarily in humans, as earlier indicated, the invention is considered to be also applicable to preventing the calcification of prostheses made from synthetic polymeric material, which material either naturally incorporates potentially chemically active groups through which covalent binding can be achieved or which can be appropriately modified so as to incorporate such groups.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

As used herein, the term "prosthesis" is meant to include any medical device that is implantable in a mammal. Thus, the term includes heart valves and other heart components, vascular replacements or grafts, artificial hearts, urinary tract and bladder replacements, bowel and tissue resections, left ventricular-assist devices, artificial tendons, and the like. However, it will be recognized by those having ordinary skill in this art that the present invention may be of most importance in relation to prostheses for which calcification after implantation has been a clinical problem.

The specific material from which the prosthesis is prepared is not critical. Thus, the prosthesis can be one which is made from natural tissues, including but not limited to bovine, ovine, porcine, and human tissue; metals; synthetic organic materials, such as polyurethanes, polyether urethanes; silicones; polyesters; polycarbonates; polyacrylates and methacrylates; polyacetates; polyolefins, such as polyethylene and polypropylene; polyalcohols; combinations and derivatives thereof; and the like. Other materials, well known to those having ordinary skill in the art, also can be used.

In general, the anticalcification agent can be any agent that imparts a hydrophobic nature to the surface of the tissue, including but not limited to the siloxane-containing agents discussed below.

One embodiment of the present invention involves the fixation with substituted dialdehydes of animal or other biological tissues for use as implantable devices.

Figure 1:
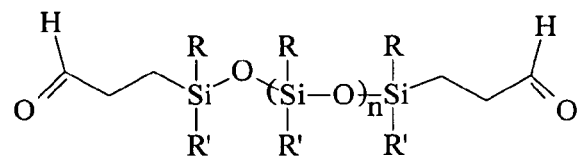
FIG. 1. General structure of a siloxane dialdehyde.

In some embodiments, the substituted dialdehydes are siloxane dialdehyde compounds that may comprise the general structure shown in FIG. 1. The simplest compound is R=R'=CH$_3$, the dimethylsiloxane repeat unit. However, other R groups can be present, such as phenyl, ethyl, isopropyl, butyl, cyanoethyl, or groups known to be present in siloxane polymers.

The siloxane dialdehydes typically have a propyl (3 carbon) end group on which the terminal aldehyde group is attached. These compounds are prepared from the corresponding carbinol derivative by oxidation of the terminal hydroxyl group. Various known methods for affecting such an oxidation of the alcohol group are well known in the art.

Figure 2:
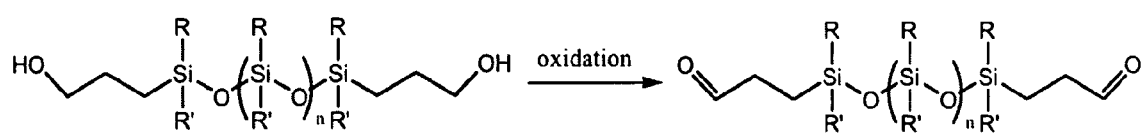
FIG. 2. Oxidation of a siloxane dicarbinol to a siloxane dialdehydes.

The compounds can be made by a straightforward oxidation of the corresponding carbinol derivative as shown in FIG. 2. Other carbon chain lengths for the end group may be used, but using a carbinol with at least three carbon atoms and the hydroxyl to be oxidized on at least the third carbon is preferable to prevent elimination by the beta silicon effect. The compound should be dissolved in a water-soluble solvent for the treatment of tissue. Solubility data for these compounds parallel closely the solubility of the corresponding carbinol compounds. The solubility decreases as the repeat unit of the siloxane chain increases.

Useful in embodiments of the present invention are substituted siloxane dialdehydes of Formula I:

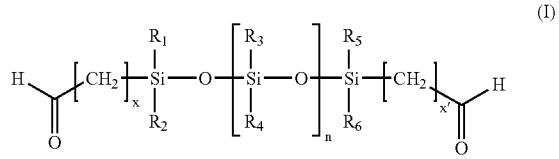

(I)

wherein R$_1$, R$_2$, R$_3$, R$_4$, R$_5$ and R$_6$ are chosen from the group consisting of alkyl, phenyl, benzyl, and cyanoethyl; wherein n=1 to 100; and wherein x and x'=2 to 30. Particularly useful in embodiments of the present invention are substituted siloxane dialehydes of Formula I wherein R$_1$=R$_2$=R$_3$=R$_4$=R$_5$=R$_6$=CH$_3$.

Figure 5:
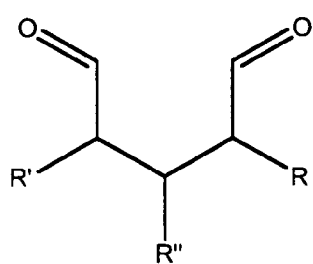
FIG. 5. General structure of an aliphatic, siloxane or fluorocarbon substituted dialdehydes.

A second embodiment of the substituted dialdehydes is the substituted dialdehydes, such as a substituted glutaraldehyde, as shown in FIG. 5. In this embodiment, R, R', and R" can either be identical or different side chains, and can be aliphatic, an aliphatic derivative, polymeric, a siloxane, or a perfluorocarbon group. The presence of these side groups are for the purpose of increasing the solubility of the dialdehydes in a supercritical fluid phase and for providing a side chain to impart anticalcification properties to the fixative. Such compounds may be synthesized through preparation of a cyclopentene molecule with the desired substituents followed by oxidation to the corresponding dialdehydes by the use of well known oxidation reactions utilizing reagents such as permanganate or ozone.

Substituted dialdehydes useful in embodiments of the present invention are substituted dialdehydes of Formula II:

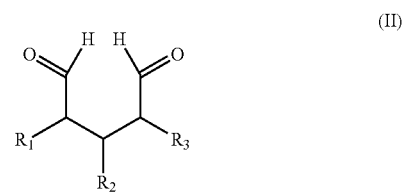

(II)

wherein R$_1$, R$_2$ and R$_3$ are chosen from the group consisting of alkyl chains, partially fluorinated alkyl chains, perfluoroalkyl chains, polyether chains and siloxane chains. Particularly useful in embodiments of the present invention are substituted dialehydes of Formula II wherein the alkyl chains, partially fluorinated alkyl chains, and said perfluoroalkyl chains, are of length C1 to C30.

The invention, in some embodiments, utilizes diamine and/or monoamines, including but not limited to siloxane and/or perfluorocarbon substituted monoamines and/or diamines.

Figure 3:
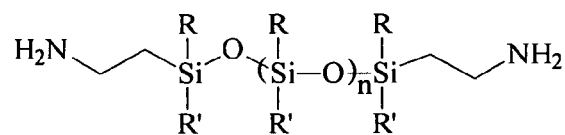
FIG. 3. General structure of a siloxane diamine.
Figure 4:
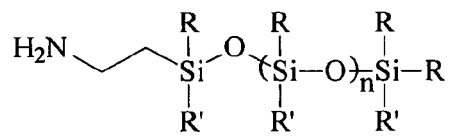
FIG. 4. General structure of a siloxane monoamine.

Siloxane diamines typically have the structure shown in FIG. 3. The simplest compound is R=R'=CH$_3$, the dimethylsiloxane repeat unit. However, other R groups can be present, such as phenyl, ethyl, isopropyl, butyl, cyanoethyl, or groups known to be present in siloxane polymers. Siloxane monoamines are also useful for terminating free aldehyde groups. An example of a siloxane monoamine is shown in FIG. 4, where the R groups are described as above.

The siloxane diamine typically has a propyl (3 carbon) end group to which the amine is attached. However, other carbon chain lengths for the end group may be used. The solubility of the siloxane diamine is very low in water with the solubility decreasing as the siloxane repeat unit increases. The use of ethanol as a solvent increases the solubility of the siloxane diamine compounds. Other solvents that are both water and organic soluble, such as diethyl ether, tetrahydrofuran, dioxane, or polar aprotic solvents such as dimethylformamide, formamide, dimethyl sulfoxide, or similar solvents could be conceivably used as a vehicle for siloxane diamines. It should be noted, however, that the siloxane diamine only requires limited solubility to be effective as an anti-calcification treatment modality, and it is also conceivable that a water emulsion of the siloxane diamine may be sufficient to block the residual aldehyde functional groups.

Siloxane diamines useful in embodiments of the present invention are substituted diamines of formula III:

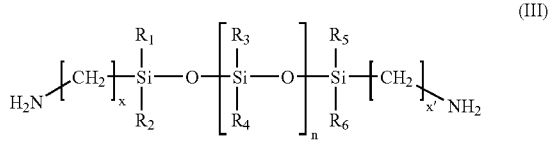

(III)

wherein R$_1$, R$_2$, R$_3$, R$_4$, R$_5$ and R$_6$ are chosen from the group consisting of alkyl, phenyl, benzyl, and cyanoethyl; wherein n=1 to 100; and wherein x and x'=2 to 30. Particularly useful in embodiments of the present invention are siloxane diamines of formula III wherein $R_1=R_2=R_3=R_4=R_5=R_6=CH_3$.

Siloxane monoamines useful in embodiments of the present invention are substituted monoamines of formula IV:

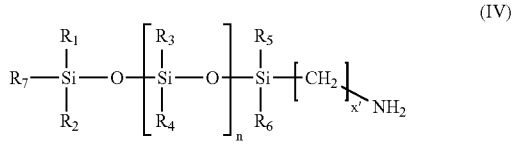

wherein $R_1$, $R_2$, $R_3$, $R_4$, $R_5$, $R_6$ and $R_7$ are chosen from the group consisting of alkyl, phenyl, benzyl, and cyanoethyl; wherein n=1 to 100; and wherein x and x'=2 to 30. Particularly useful in embodiments of the present invention are siloxane diamines of formula IV wherein $R_1=R_2=R_3=R_4=R_5=R_6=R_7=CH_3$.

Table 1 presents the solubility of a variety of siloxane diamines.

TABLE 1

| | | Solubility of Various Siloxane Diamines | | | |
|---|---|---|---|---|---|
| Sample | Viscosity | 100% Ethanol | 95/5 Ethanol/$H_2O$ | 93/7 Ethanol/$H_2O$ | 90/10 Ethanol/$H_2O$ |
| A11 | 10-15 cSt | 9%, sol | 10%, sol | 1% sol; 10% emul | 10%, emul |
| A12 | 20-30 cSt | 9%, sol | 3%, 5% emul | NS | NS |
| A15 | 50-60 cSt | 1%, emul | NS | NS | NS |
| A21 | 100-120 cSt | 1%, emul | NS | NS | NS |
| A32 | 2000 cSt | 1%, emul | NS | NS | NS |

Sol = soluble
Emul = emulsion
NS = not soluble

In certain embodiments the fixatives and agents of the present invention may be provided in the form of either solution, emulsions or suspensions in suitable liquid media.

Overall the present invention provides processes comprising the steps of providing a biological tissue, fixing the tissue with a fixative, and treating the tissue with an agent that creates a hydrophobic environment on the tissue such that the hydrophobic environment prevents calcification of the tissue while retaining biocompatibility. In certain embodiments the steps of these processes are performed sequentially while in other embodiments the steps are performed simultaneously. Also, the present invention provides new and useful materials and products prepared by these processes.

Those of skill in the art will understand how to obtain and prepare appropriate perfluorocarbon diamines and monoamines.

EXAMPLES

The following examples are included to demonstrate preferred embodiments of the invention. It should be appreciated by those of skill in the art that the techniques disclosed in the following examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fixation of tissue, for example, but not limited to, bovine or porcine pericardial tissue, is accomplished by dissolving the reactive substituted dialdehyde compounds described above and known to those of skill in a solvent system that allows the substituted dialdehydes to penetrate the moist tissue for complete fixation. Such a solvent by nature is a polar, water compatible solvent such as tetrahydrofuran, formamide, dimethyl formamide, 2-methoxyethanol, dioxane, or other water compatible solvent that is also a solvent for the substituted dialdehydes. In some cases, the supercritical $CO_2$ solvents discussed below may be used in this regard.

The tissue is first added to the solvent to remove water from the tissue. The tissue can then be removed and placed in contact with more solvent containing the substituted dialdehyde or other fixative and allowed to stand for a period of time from hours to days. The temperature of the fixation is not critical, but can vary from refrigerated temperatures to approximately 80° F. without causing undesirable changes in the tissue.

Example 2

Post-fixation treatment of glutaraldehyde fixed tissue is accomplished in a manner similar to that described in Example 1. Siloxane and/or perfluorocarbon amine compounds, for example siloxane monoamines or diamines can be dissolved in a solvent system that allows the siloxane dialdehydes to penetrate the moist tissue for complete fixation. Such a solvent by nature is typically a polar, water compatible solvent such as tetrahydrofuran, formamide, dimethyl formamide, 2-methoxyethanol, dioxane, or other water compatible solvent that is also a solvent for the siloxane dialdehydes. Of course, the supercritical $CO_2$ solvents discussed below may be used in this regard.

The tissue is first added to the solvent to remove water from the tissue, decanted, and then solvent containing the siloxane amines is added to the tissue and allow to stand for a period of time from hours to days. The temperature of the fixation is not critical, but can vary from refrigerated temperatures to approximately 80° F. without causing undesirable changes in the tissue.

Example 3

In some embodiments of the invention, one can fix fresh tissue by using supercritical $CO_2$ (sc$CO_2$) with soluble additives for fixation in a supercritical fluid process, and treating fixed tissue using a sc$CO_2$ additive to reduce calcification potential. More specifically, one can use supercritical fluid additives containing siloxane or perfluorocarbon segments as described herein with terminal aldehyde groups for tissue fixation or terminal amine groups for reducing calcification potential. For example, one can use sc$CO_2$ in conjunction with a siloxane and/or perfluorocarbon dialdehyde to fix tissue and place a siloxane group in a position on the tissue where it can prevent calcification. Alternatively, one can use sc$CO_2$ in conjunction with other fixatives, such as glutaraldehyde or a derivative of glutaraldehyde, to fix tissue prior to treatment with a composition, such as a siloxane diamine.

To treat tissue with longer chain dialdehydes, solvents other than water are required due to the decreasing solubility with chain length. With the very hydrophobic siloxane segment, the corresponding dialdehydes have virtually zero solubility in aqueous solution, and thus a second solvent media is required. Alcohols, ethers, and other polar aprotic solvents tend to be solvents for these types of compounds. There are significant advantages, however, to using sc$CO_2$ over other solvents, such as lack of toxicity and residuals from SCF processing steps. A second advantage is the low viscosity and high diffusion coefficient of sc$CO_2$, which may allow greater penetration of the solvent (and fixative) into the interior of the tissue leading to greater fixation efficiency and greater tissue stabilization. The unique solubility behavior of the siloxane segment or perfluorocarbon segment in sc$CO_2$ allows tissue to be fixed and yet provide hydrophobic character that may then reduce or prevent the deposition of calcium phosphate within the tissue, which ultimately leads to failure of bioprostheses made from fixed tissue.

A second application of sc$CO_2$ is in treating glutaraldehyde fixed tissue with amine containing reagents to block residual aldehyde functionality. By using a diamine with siloxane segment as the main component of the molecule, the solubility of these compounds are increased significantly in supercritical $CO_2$, as it is well known that supercritical $CO_2$ is a very good solvent for poly(dimethylsiloxanes). A siloxane monoamine would also be advantageous for blocking free aldehyde groups and adding hydrophobicity to the surface of the tissue. For a monoamine, one end of the siloxane would be terminated with an trimethylsilyl group rather than a dimethyl (3-amino)propyl silyl group.

Example 4

There are a variety of manners in which one can measure calcification and whether or not a given anti-calcification treatment or agent is effective to prevent calcification of a tissue.

Calcification of tissues is characterized by the way in which the calcium crystals form in relation to the sample. In in vivo models, calcification tends to be intrinsic, where the calcium crystals form within the tissue, grow, and then break through the external surface of the tissue. Extrinsic calcification also occurs with in-vivo models, but to a lesser extent than intrinsic calcification. With in vitro models, calcification tends to be mainly extrinsic.

Samples for assaying calcification, are obtained from fresh bovine or porcine pericardial sacs or other tissue from an abattoir. Typically, such samples are shipped within 24 hr of harvesting and stored at $0°$ C. Upon receipt of the samples, they are fixed in an appropriate manner. For assays in which post-fixation techniques of prevention of calcification are to be studied, one can process the tissue with glutaraldehyde in the following manner. Tissue samples for fixation can first be rinsed in isotonic saline buffered at pH 7.4. Fixation can then be performed by placing the tissue in a fresh solution of 0.5% glutaraldehyde for 24 hours at room temperature, rinsing the tissue, then placing the tissue in a 0.2% glutaraldehyde solution. The treated tissue can then be stored at $8°$ C. until further treatment.

In order to assay for the ability of a compound, such as siloxane dialdehyde, to serve as a combined fixative and anti-calcification agent, one can obtain tissues as discussed above, and then fix them in much the manner described for glutaraldehyde, but substitute the putative fixative/anticalcification agent for the glutaraldehyde. Of course, those of skill will be able to modify and adjust these techniques according to the needs of the given substances to be tested for anticalcification activity.

In Vitro Calcification Assay Methods

One can assay calcification in vitro using a passive system of calcification. In this regard, calcium deposits are typically formed on samples in a metastable calcium phosphate solution. These deposits formed during in vitro tests tend to differ from those in living tissue. In living tissue deposits of calcium phosphate form but are then converted to hydroxyapatite. In in vitro tests, the deposits are only calcium phosphate. One can prepare a calcium containing solution for an assay by preparing a metastable calcium phosphate. One centimeter disks of glutaraldehyde fixed bovine or porcine tissue can be cut from a larger section. These disks can be treated with any of a number of treated samples by soaking them in a metastable calcium phosphate solution at $37°$ C. Samples can be incubated over an eight week period and then analyzed by for calcium by ICP (Inductably-Coupled Plasma Mass Spectroscopy) after nitric acid ashing.

It is possible to conduct in vivo studies of calcification with subcutaneous rat implant studies. Samples are prepared as described above, randomized and placed subcutaneously in the dorsal quadrants of six week old Sprague Dawley Rats. After four to eight weeks, the samples are explanted. Samples are then analyzed for calcium content by ICP as described above.

All of the formulations, compositions, methods and processes disclosed and claimed herein can be made and executed without undue experimentation in light of the present disclosure. While the formulations, compositions, methods and processes of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

We claim:

1. A process comprising the steps of:
   i. providing a biological tissue,
   ii. fixing the tissue with a fixative;
   iii. treating the tissue with an agent that creates a hydrophobic environment on said tissue wherein said hydrophobic environment prevents calcification of said tissue while retaining biocompatibility wherein the agent is selected from the group consisting of a siloxane dialdehyde of the structure

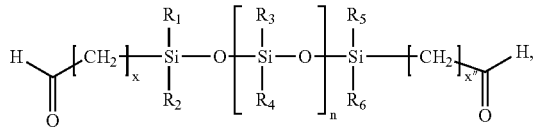

a dialdehyde of the structure

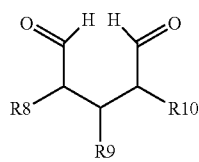

a siloxane diamine of the structure

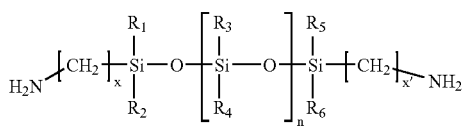

and a siloxane monoamine of the structure

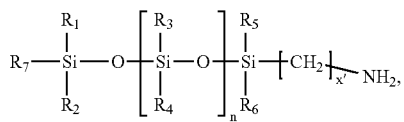

wherein $R_1$, $R_2$, $R_3$, $R_4$, $R_5$, $R_6$ and $R_7$ are chosen from the group consisting of alkyl, phenyl, benzyl, and cyanoethyl; wherein n=1 to 100; wherein x and x'=2 to 30; and wherein $R_8$, $R_9$ and $R_{10}$ are chosen from the group consisting of alkyl chains, partially fluorinated alkyl chains, perfluoroalkyl chains, polyether chains and siloxane chains.

2. The process of claim 1, wherein step ii. and step iii. are performed simultaneously.

3. The process of claim 1, wherein step ii. and step iii. are performed sequentially.

4. The process of claim 1, wherein said agent used to treat the tissue to prevent calcification also fixes the tissue.

5. The process of claim 1, wherein $R_1=R_2=R_3=R_4=R_5=R_6=CH_3$.

6. The process of claim 1, wherein said alkyl chains, said partially fluorinated alkyl chains, and said perfluoroalkyl chains, are of length C1 to C30.

7. The process of claim 1, wherein said agent comprises a solution, emulsion or suspension in a suitable liquid medium.

8. The process of claim 7, wherein said a suitable liquid medium is supercritical $CO_2$.

9. The process of claim 7, wherein said a suitable liquid medium is an aprotic polar solvent.

10. The process of claim 7, wherein said a suitable liquid medium is an alcohol.

11. The process of claim 1, wherein said fixative comprises a solution, emulsion or suspension in a suitable liquid medium.

12. The process of claim 11, wherein said a suitable liquid medium is supercritical $CO_2$.

13. The process of claim 11, wherein said a suitable liquid medium is an aprotic polar solvent.

14. The process of claim 11, wherein said a suitable liquid medium is an alcohol.

* * * * *